US011247201B2

United States Patent
Al-Nezari et al.

(10) Patent No.: US 11,247,201 B2
(45) Date of Patent: Feb. 15, 2022

(54) LIGANDS FOR PRODUCTION OF 1-HEXENE IN CHROMIUM ASSISTED ETHYLENE OLIGOMERIZATION PROCESS

(71) Applicant: SABIC Global Technologies B.V., Bergen op Zoom (NL)

(72) Inventors: Abdulaziz Al-Nezari, Thuwal (SA); Balamurugan Vidjayacoumar, Thuwal (SA); Ilia Korobkov, Thuwal (SA); Khalid Albahily, Thuwal (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/292,285

(22) PCT Filed: Nov. 11, 2019

(86) PCT No.: PCT/IB2019/059672
§ 371 (c)(1),
(2) Date: May 7, 2021

(87) PCT Pub. No.: WO2020/100010
PCT Pub. Date: May 22, 2020

(65) Prior Publication Data
US 2022/0001368 A1 Jan. 6, 2022

Related U.S. Application Data

(60) Provisional application No. 62/758,809, filed on Nov. 12, 2018.

(51) Int. Cl.
*B01J 31/02* (2006.01)
*B01J 31/14* (2006.01)
*C07C 2/34* (2006.01)

(52) U.S. Cl.
CPC ......... *B01J 31/0265* (2013.01); *B01J 31/143* (2013.01); *C07C 2/34* (2013.01); *B01J 2231/20* (2013.01); *B01J 2531/62* (2013.01); *C07C 2531/18* (2013.01); *C07C 2531/22* (2013.01); *C07C 2531/34* (2013.01)

(58) Field of Classification Search
None
See application file for complete search history.

(56) References Cited

U.S. PATENT DOCUMENTS

2017/0203288 A1* 7/2017 Al-Hazmi .............. B01J 31/143

FOREIGN PATENT DOCUMENTS

WO    WO 2016/012948    1/2016

OTHER PUBLICATIONS

International Search Report and Written Opinion issued in Corresponding PCT Application No. PCT/IB2019/059672, dated Jan. 28, 2020.

(Continued)

*Primary Examiner* — Ali Z Fadhel
(74) *Attorney, Agent, or Firm* — Norton Rose Fulbright US LLP

(57) ABSTRACT

Catalyst compositions and processes for the oligomerization of ethylene to 1-hexene are described. The catalyst composition includes a triamino bisphospino (NPNPN) ligand system with specific phosphorous and nitrogen ligands. The terminal nitrogen atoms include linear alkyl hydrocarbons that differ in the number of carbon atoms by 3.

20 Claims, 1 Drawing Sheet

(56) References Cited

OTHER PUBLICATIONS

Jefferson et al., "Formation of cyclophosph(III)azanes and their oxo- and thioxo-derivatives" *J. Chem. Soc. Dalton Trans.* 1973, 13, 1414-1419.

Peulecke et al., "Ligands with an NPNPN-framework and their application in chromium catalysed ethane tri-/tetramerization" *Dalton Trans.* 2016, 45, 8869-8874.

* cited by examiner

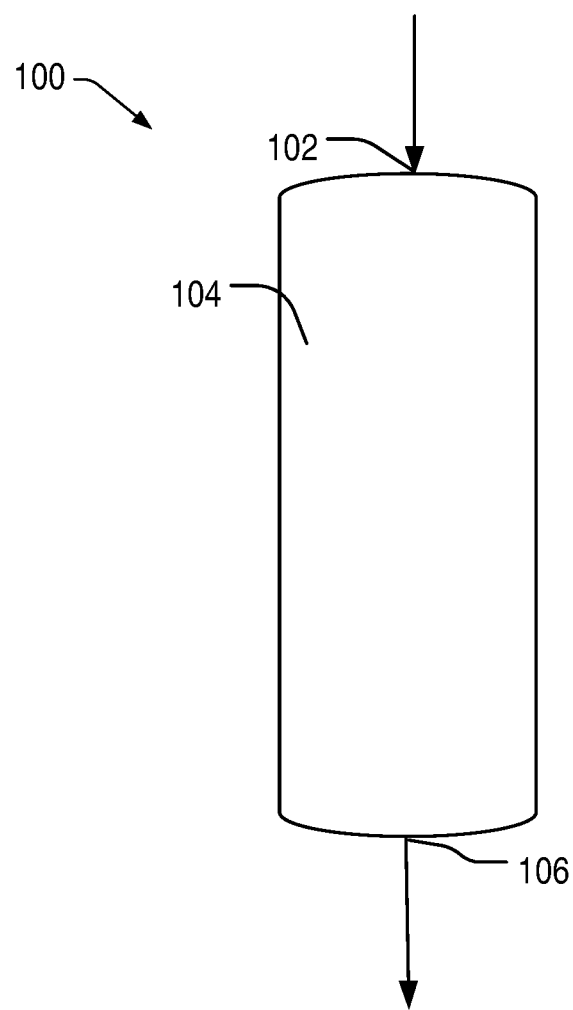

LIGANDS FOR PRODUCTION OF 1-HEXENE IN CHROMIUM ASSISTED ETHYLENE OLIGOMERIZATION PROCESS

CROSS REFERENCE TO RELATED APPLICATIONS

This application is a national phase application under 35 U.S.C. § 371 of International Application No. PCT/IB2019/059672, filed Nov. 11, 2019, which claims the benefit of priority to U.S. Provisional Patent Application No. 62/758,809, filed Nov. 12, 2018, the entire contents of each of which are hereby incorporated by reference in their entirety.

BACKGROUND OF THE INVENTION

A. Field of the Invention

The invention generally concerns a catalyst for the oligomerization of ethylene to 1-hexene. The catalyst includes a chromium (III) species and a ligand that promotes oligomerization selectivity of 1-hexene over 1-octene.

B. Description of Related Art

Existing processes for the production of linear alpha olefins (LAOs), including comonomer-grade 1-butene, 1-hexene, and 1-octene, rely on the oligomerization of ethylene, and can lead to a mixture of ethylene-derived oligomers having a chain length of 4, 6, 8, and so on. Without being bound by theory, it is believed that this is due to a chemical mechanism mainly governed by competing chain growth and displacement reaction steps, leading to a Schulz-Flory- or Poisson-product distribution. From a commercial standpoint this product distribution poses a challenge for the full-range LAO producer as each served market segment can exhibit a different behavior in terms of market size and growth, geography, fragmentation etc. It is, therefore, difficult for the LAO producer to adapt to the market requirements due to part of the product spectrum might be in high demand in a given economic context, while at the same time, other product fractions might not be marketable at all or only in a marginal niche. For example, certain grades of polyethylene materials call for modified physical properties such as modified tensile strength and crack resistance, requiring the presence of 1-hexene, but not other ethylene-derived oligomers.

Oligomerization of ethylene usually proceeds in the presence of suitable catalysts. Several of the existing ethylene oligomerization, i.e., dimerization, trimerization or tetramerization, catalysts have one or more disadvantages. These disadvantage can include: 1) low selectivity for the desirable products; 1-hexene); 2) low selectivities for the LAO isomer within the $C_6$ cut (e.g., isomerization, branched olefin formation etc.); 3) wax formation (e.g., formation of heavy, long-chain (high carbon-number) products); 4) polymer formation (polyethylene, including branched and/or cross-linked PE) that can lead to considerable LAO product yield loss as well as fouling of equipment; 5) poor turnover rates/catalyst activity, resulting in increased cost per kg product; 6) high catalyst- or ligand cost; 7) complex, multi-step ligand synthesis, resulting in poor catalyst availability and high catalyst cost; 8) susceptibility of catalyst performance, both in terms of both activity and selectivity, to trace impurities (leading to, for example, catalyst losses/-poisoning); 9) difficult handling of catalyst components in a technical/commercial environment (e.g., during catalyst complex synthesis, pre-mixing, inertization, catalyst recovery, or ligand recovery); 10) harsh reaction conditions, for example high temperatures and pressure, resulting in a need for special equipment (increased investment-, maintenance-, and energy costs); 11) high co-catalyst/activator cost or consumption; and/or 12) susceptibility to varying co-catalyst qualities, which is often the case when larger amounts of relatively ill-defined compounds are used as activators (e.g., certain methylaluminoxane (MAO)-varieties).

Attempts to produce LAOs have been described. By way of example, U.S. Patent Application Publication No. 2017/0203288 to Al-Hazmi et al. describes the use of a catalyst composition that can include a chromium compound and an functionalized triamino, diphosphine (NPNPN) ligand of the formula $(R^1)$ $(R^2)N—P(R^3)—N(R^4)—P(R^5)—N(R^6)(R^7)$, wherein $R^1$, $R^2$, $R^3$, $R^4$, $R^5$, $R^6$, and $R^7$ are each independently hydrogen, halogen, amino, tri-methylsilyl or $C_1$-$C_{20}$ hydrocarbyl, preferably straight-chain or branched $C_1$-$C_{10}$ alkyl, phenyl, $C_6$-$C_{20}$ aryl or $C_6$-$C_{20}$ alkyl-substituted phenyl. This catalyst suffers in that it produces about a greater than 8 wt. % $C_{10+}$, and about a 50:50 wt. % ratio of 1-hexene to 1-octene. When the ratio increases to favor $C_6$ to $C_8$, the amount of $C_{10+}$ also increases, thus lowering the overall amount of desired product. In yet another example, Peulecke (*Dalton Transactions*, 2016 45; 8869-8874) describes the production of mixtures of 1-hexene and 1-octene using a NPNPN ligand of the formula $(R^1)(R^2)N—P(Ph)—N(R^3)—P(PH)—N(R^4)(R^5)$. This catalyst system suffers in that greater than 11 wt. % $C_{10+}$ is produced and the production of $C_{10+}$ hydrocarbons increases as the yield of 1-octene increases over the yield of 1-hexene.

There accordingly remains a need in the art for catalyst systems for the oligomerization of ethylene that can yield 1-hexene with high selectivity and purity.

SUMMARY OF THE INVENTION

A discovery has been made that provides a solution to at least some of the problems associated with the oligomerization of ethylene to 1-hexene. The solution is premised on the use of a $NPN(CH_3)PN$ ligand system having specific terminal amine alkyl substituents and phosphorous. Notably, the phosphorous substituents are limited to substituents that may be the same or different and selected from the group consisting of (i) $C_3$ to $C_4$ non-cyclic aliphatic groups, (ii) $C_5$ to $C_7$ aliphatic groups which may be cyclic or non-cyclic, linear or branched, substituted or unsubstituted, and (iii) any combination thereof; and preferably to cyclohexyl groups, and the terminal amines include linear alkyl groups that differ in length by 3 carbon atoms. As illustrated in a non-limiting way in the Examples, it was surprising found that limiting the substituents of the phosphorous atoms to substituents that may be the same or different and are selected from the group consisting of (i) $C_3$ to $C_4$ non-cyclic aliphatic groups, (ii) $C_5$ to $C_7$ aliphatic groups which may be cyclic or non-cyclic, linear or branched, substituted or unsubstituted, and (iii) any combination thereof; and preferably to cyclohexyl groups, and the length of the hydrocarbon chain on the terminal nitrogen atoms produces at least 80 wt. % 1-$C_6$ hydrocarbon at a selectivity of greater than 99%, 1-hexene and less than 3 wt. % solvent insoluble material (e.g., $C_{10+}$) material.

In one aspect of the present invention, catalyst compositions for the oligomerization of ethylene to 1-hexene are described. A catalyst composition can include a chromium (III) species and a ligand having the formula of:

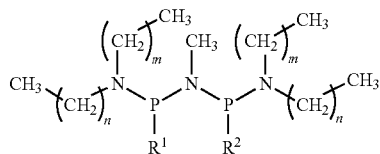

where $R^1$ and $R^2$ are the same or different and are selected from the group consisting of (i) $C_3$ to $C_4$ non-cyclic aliphatic groups, (ii) $C_5$ to $C_7$ aliphatic groups which may be cyclic or non-cyclic, linear or branched, substituted or unsubstituted, and (iii) any combination thereof; and, wherein n is 0 or 1, and m=n+3. In some embodiments, $R^1$ and $R^2$ are each independently a cyclohexyl group or an alkyl substituted cyclohexyl group, preferably both are cyclohexyl groups. In one instance, n is 0 and the catalyst is $(CH_3)(n\text{-}C_4H_9)NP(C_6H_{11})N(CH_3)NP(C_6H_{11})N(CH_3)(n\text{-}C_4H_9)$ represented by the following structure:

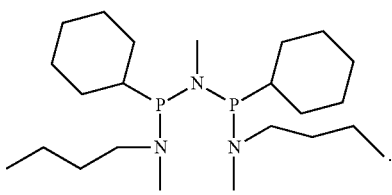 [SMILES: CCCCN(C)P(C1CCCCC1)N(C)P(C1CCCCC1)N(C)CCCC]

In another instance, n is 1 and the catalyst is $(CH_3CH_2)(n\text{-}C_5H_{11})NP(C_6H_{11})N(CH_3)NP(C_6H_{11})N(CH_2CH_3)(n\text{-}C_5H_{11})$ represented by the following structure:

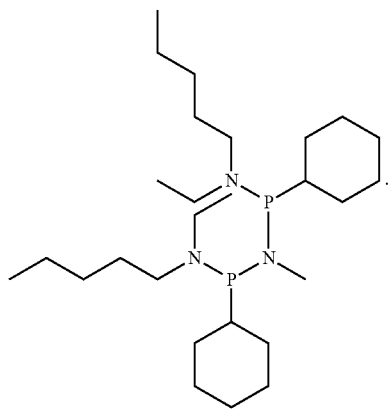 [SMILES: CCCCCN(CC)P(C1CCCCC1)N(C)P(C1CCCCC1)N(CC)CCCCC]

The catalyst composition can also include an activator or co-catalyst (e.g., methylaluminoxane compounds, preferably, methyl iso-butyl aluminum oxide compound). Chromium (III) species can include any inorganic or organic chromium compound where chromium has a valance of +3. Non-limiting examples of chromium (III) species include chromium (III) acetylacetonate, $Cr(2,2,6,6,\text{-tetramethyl-}3,5\text{-heptadionate})_3$, chromium(III)2-ethylhexanoate, chromium trichloride tris-tetrahydrofuran; chromium (III) octanoate; chromium (III) naphthenate, or any combination thereof.

Processes for producing 1-hexene using the catalyst composition of the present invention are also described. A process to produce 1-hexene can include contacting a reactant stream comprising an olefin source with a solution comprising the catalyst composition of the present invention to produce an oligomer composition that includes 1-hexene. The catalyst composition can also include a solvent (e.g., a saturated hydrocarbon, preferably n-hepane, an aromatic hydrocarbon, preferably toluene, methylcyclohexane, or a mixture thereof). The contacting step can include a temperature of 15° C. to 100° C., preferably 40° C. to 70° C. and/or a pressure of at least 2 MPa or 2 to 20 MPa, preferably 2 to 7 MPa. During the process, solvent insoluble material (e.g., polymeric material) can be produced at less than 2 wt. %, preferably less than 5 wt. % or more preferably less than 0.5 wt. %, or not at all). In some instances, the catalyst composition can include

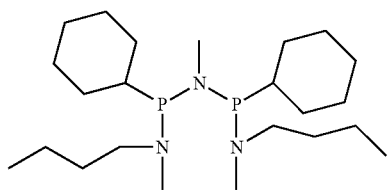

a chromium (III) species, and an activator or a co-catalyst. In other instances, the catalyst composition can include

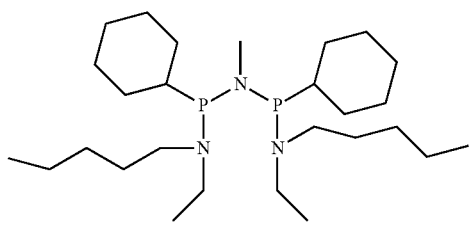

the chromium (III) species, and the activator or co-catalyst. In some embodiments, the product stream can include 1-octene. In such embodiments, the reaction selectivity for 1-hexene can be greater than 80%, and/or a weight ratio of 1-octene to 1-hexene can be less than 0.25.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions of the invention can be used to achieve methods of the invention.

The following includes definitions of various terms and phrases used throughout this specification.

The term "aliphatic" means an organic functional group or compound containing carbon and hydrogen joined together in straight chains, branched chains, or non-aromatic rings.

The term "alkyl group" refers to a linear or a branched saturated hydrocarbon. Non-limiting examples of alkyl groups include methyl, ethyl, propyl, butyl, pentyl, etc.

An "aryl" group or an "aromatic" group is a substituted or substituted, mono- or polycyclic hydrocarbon with alternating single and double bonds within each ring structure.

Non-limiting examples of aryl group substituents include alkyl, substituted alkyl groups, linear or branched alkyl groups, linear or branched unsaturated hydrocarbons, halogen, hydroxyl, alkoxy, haloalkyl, haloalkoxy, carboxylic acid, ester, amine, nitro, amide, nitrile, acyl, alkyl silane, thiol and thioether substituents. Non-limiting examples of alkyl groups include linear and branched $C_1$ to $C_5$ hydrocarbons. Non-limiting examples of unsaturated hydrocarbons include $C_2$ to $C_5$ hydrocarbons containing at least one double bond (e.g., vinyl). The aryl or alkyl group can be substituted with the halogen, hydroxyl, alkoxy, haloalkyl, haloalkoxy, carboxylic acid, ester, ether, amine, nitro (—$NO_2$), amide, nitrile (—CN), acyl, alkyl silane, thiol and thioether substituents. Non-limiting examples of halogens include chloro (—Cl), bromo (—Br), or fluoro (—F) substituents. Non-limiting examples of haloalkyl substituents include —$CX_3$, —$CH_2X$, —$CH_2CH_2X$, —$CHXCH_2X$, —$CX_2CHX_2$, —$CX_2CX_2$ where X is F, Cl, Br or combinations thereof. Non-limiting examples, of amine substituents include —$NH_2$, —$CH_2NH_2$, —$CHCH_2NH_2$, —$C(NH_2)CH_3$. Non-limiting examples of alkoxy include —$OCH_3$, —$OCH_2CH_3$, and the like. Non-limiting examples, of alkyl silane substituents include —$Si(CH_3)_3$, —$Si(CH_2CH_3)_3$, and the like. Non-limiting examples of polycyclic groups include ring systems that include 2 or more conjugated rings (e.g., fused aromatic rings) and substituted conjugated rings such as —$C_{10}H_7$ and substituted ten carbon conjugated ring systems.

A "$C_3$ to $C_4$ non-cyclic aliphatic group" means a non-cyclic hydrocarbon group containing 3 or 4 carbon atoms, with non-limiting examples including iso-propyl and tert-butyl. A "$C_5$ to $C_7$ group" is a hydrocarbon group containing 6, 7, or 8 carbon atoms, with non-limiting examples including pentyl, hexyl, heptyl, and cyclohexyl. A "$C_5$ to $C_7$ substituted or unsubstituted cycloalkane group" means a substituted or unsubstituted, cyclic hydrocarbon group containing 6, 7, or 8 carbon atoms, with non-limiting examples including cyclopentyl, cyclohexyl, and cycloheptyl. When fully saturated with hydrogen and having the formula $C_5H_9$, $C_6H_{11}$, $C_7H_{13}$, it is a $C_5$ to $C_7$ unsubstituted cycloalkane group. When at least one of the hydrogen atoms is replaced by another atom or functional group, it is a $C_5$ to $C_7$ substituted cycloalkane group.

A "cyclohexyl" group is a substituted or unsubstituted, cyclic hydrocarbon group containing 6 carbon atoms. When fully saturated with hydrogen and having the formula $C_6H_{11}$, the cyclohexyl group is an unsubstituted cyclohexyl group. When at least one of the hydrogen atoms is replaced by another atom or functional group, the cyclohexyl group is an substituted cyclohexyl group.

The phrase "solvent insoluble" refers to polymer material with the molecular weight 500 g/mol and above (30+ carbon atoms) and is present in amounts of less than <2 wt. %, preferably <1 wt. %, more preferably <0.5 wt. % as determined gravimetrically.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %", "vol. %", or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalyst compositions of the present invention can "comprise," "consist essentially of," or "consist of" particular ingredients, components, compositions, etc. disclosed throughout the specification. With respect to the transitional phrase "consisting essentially of," in one non-limiting aspect, a basic and novel characteristic of the catalyst compositions of the present invention are their abilities to catalyze the oligomerization of ethylene to 1-octene in greater than 80% selectivity with the production of minimal amounts of solvent insoluble material (e.g., <3 wt. %).

In the context of the present invention at least twenty embodiments are now described. Embodiment 1 is a catalyst composition for the oligomerization of ethylene to 1-hexene. The catalyst composition contains a chromium (III) species; and a ligand having the formula of:

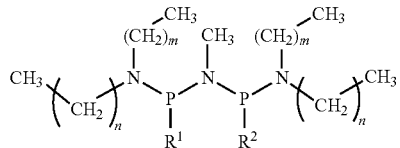

where $R^1$ and $R^2$ are the same or different and are selected from the group consisting of (i) $C_3$ to $C_4$ non-cyclic aliphatic groups, (ii) $C_5$ to $C_7$ aliphatic groups which may be cyclic or non-cyclic, linear or branched, substituted or unsubstituted, and (iii) any combination thereof; and, wherein n is 0 or 1, and m=n+3. Embodiment 2 is the catalyst composition of embodiment 1, wherein $R^1$ and $R^2$ are each independently a cyclic hydrocarbon group, a substituted cyclic hydrocarbon group, a linear hydrocarbon group or a branched hydrocarbon group having 1 to 10 carbon atoms. Embodiment 3 is the catalyst composition of embodiment 2, wherein R1 and R2 are each a cyclohexyl group. Embodiment 4 is the catalyst composition of embodiment 3, wherein n is 0, and the catalyst has the structure of:

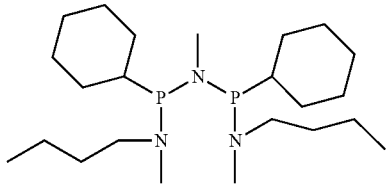

Embodiment 5 is the catalyst composition of embodiment 3, wherein n is 1 and the catalyst has the structure of

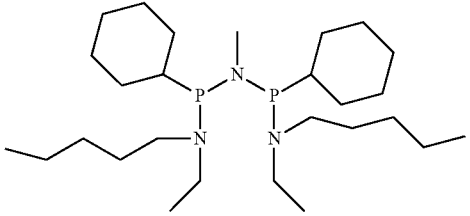

Embodiment 6 is the catalyst composition of any one of embodiments 1 to 5, wherein the composition further contains an activator or co-catalyst. Embodiment 7 is the catalyst composition of embodiment 6, wherein the activator or co-catalyst is a methylaluminoxane compound. Embodiment 8 is the catalyst composition of embodiment 6, wherein the activator or co-catalyst is a methyl iso-butyl aluminum oxide compound. Embodiment 9 is the catalyst composition of embodiment 1, wherein the chromium (III) species is selected from the group consisting of chromium (III) acetylacetonate, Cr(2,2,6,6,-tetramethyl-3,5-heptadionate)$_3$, chromium(III)2-ethylhexanoate, chromium trichloride tris-tetrahydrofuran; (benzene)tricarbonyl chromium; chromium (III) octanoate and chromium (III) naphthenate. Embodiment 10 is the catalyst composition of embodiment 1, wherein one or both of $R^1$ and $R^2$ are selected from the group consisting of iso-propyl and tert-butyl. Embodiment 11 a process to produce 1-hexene from ethylene, the process including the steps of contacting a reactant stream containing an olefin source with a solution comprising the catalyst composition of any one of embodiments 1 to 9 to produce a oligomer composition comprising 1-hexene. Embodiment 12 is the process of embodiment 11, wherein the solution includes a solvent. Embodiment 13 is the process of embodiment 12, wherein the solvent is a saturated hydrocarbon. Embodiment 14 is the process of embodiment 13, wherein the solvent is n-hexane, methylcyclohexane, or a mixture thereof. Embodiment 15 is the process of any one of embodiments 11 to 14, wherein the product stream further includes 1-octene and a selectivity for 1-hexene is greater than 99%, and a weight ratio of 1-octene to 1-hexene is less than 0.15. Embodiment 16 is the process of embodiment 15, wherein the catalyst composition contains

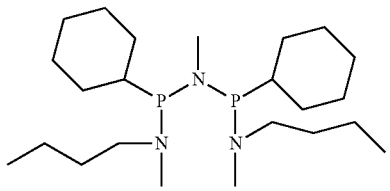

Embodiment 17 is the process of any one of embodiment 15, further including the chromium (III) species, the activator or co-catalyst. Embodiment 18 is the process of any one of embodiment 11 to 17, wherein the catalyst composition contains the chromium (III) species, the activator or co-catalyst and

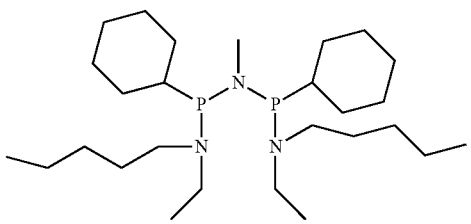

Embodiment 19 is the process of any one of embodiments 11 to 18, wherein the contacting includes a temperature of 15° C. to 100° C., preferably 40° C. to 70° C. Embodiment 20 is the process of any one of embodiments 11 to 19, wherein the contacting is conducted at a pressure of at least 2 MPa or 2 to 20 MPa, preferably 2 to 7 MPa.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

FIG. 1 is an illustration of a schematic of a system to produce 1-hexene from the oligomerization of ethylene.

While the invention is susceptible to various modifications and alternative forms, specific embodiments thereof are shown by way of example in the drawings. The drawings may not be to scale.

DETAILED DESCRIPTION OF THE INVENTION

A discovery has been made that provides a way to produce 1-hexene in acceptable yields, in high selectivity, and without making significant amounts of solvent insoluble material from the oligomerization of ethylene. The discovery is premised on using a NPNPN ligand system. Notably, and as illustrated in a non-limiting manner in the examples, an oligomerization product stream can include at least 80 wt. % $C_6$ hydrocarbon, less than 10 wt. % $C_8$ hydrocarbon, and less than 3 wt. % solvent insoluble material (e.g., polymeric materials). This is contrast to the ligands of the prior art, which produce more than 3 wt. % polymeric materials. The critical parameters include the choice of phosphorous substituents and nitrogen substituents. The phosphorous substituents include an aromatic group or an alkyl substituted aromatic group, the middle nitrogen substituent includes a methyl substituent, and the terminal nitrogen substituents include different linear alkyl hydrocarbons groups that differ in the number of carbon atoms by 3. This combination of substituents provides an elegant and simple ligand system for the production of 1-hexene in high purity and selectivity above 80 wt. %.

These and other non-limiting aspects of the present invention are discussed in further detail in the following sections.

A. Catalyst Composition

The catalyst composition can include the ligands of the present invention, a chromium (III) species, and an activator or co-catalyst. The ligands of the present invention can be prepared as described throughout the specification and in the Examples. The catalyst composition can be provided as a solution in an aliphatic or aromatic hydrocarbon solvent. Aliphatic hydrocarbon solvents can include hexane, methylcyclohexane, cyclohexane, n-heptane and the like.

The ligands of the present invention can be represented by the following formula:

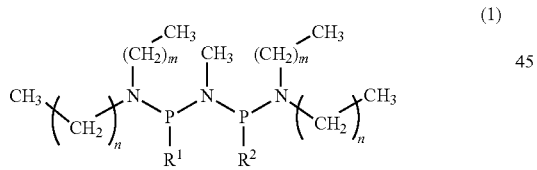
(1)

where $R^1$ and $R^2$ selected from the group consisting of (i) $C_3$ to $C_4$ non-cyclic aliphatic groups, (ii) $C_5$ to $C_7$ aliphatic groups which may be each be cyclic or non-cyclic, linear or branched, substituted or unsubstituted, and (iii) any combination thereof, and wherein n is 0 or 1, and m=n+3. The $C_5$ to $C_7$ aliphatic groups can substituted or unsubstituted cycloalkane groups include cyclopentyl, cyclohexyl, cycloheptyl, substituted cyclopentyl, substituted cyclohexyl, and substituted cycloheptyl. The $C_3$ to $C_4$ non-cyclic aliphatic groups can be iso-propyl and tert-butyl. The ligands can be $(CH_3)(n-C_4H_9)NP(R^1)N(CH_3)NP(R^2)N(CH_3)(n-C_4H_9)$ and $(CH_3CH_2)(n-C_5H_{11})NP(R^1)N(CH_3)NP(R^2)N(CH_2CH_3)(n-C_5H_{11})$ $(CH_3)(n-C_4H_9)NP(C_6H_{11})N(CH_3)NP(C_6H_{11})N(CH_3)(n-C_4H_9)$ and $(CH_3CH_2)(n-C_5H_{11})NP(C_6H_{11})N(CH_3)NP(C_6H_{11})N(CH_2CH_3)(n-C_5H_{11})$. The structure of the ligands can be illustrated as follows:

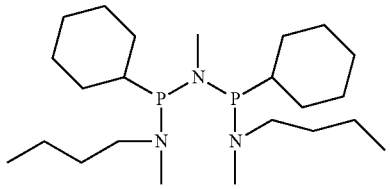
(2)

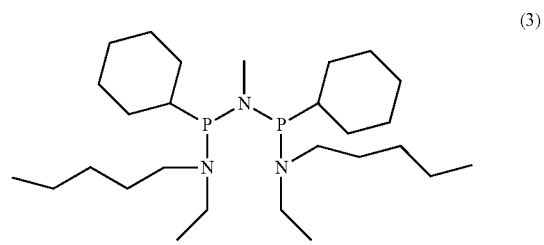
(3)

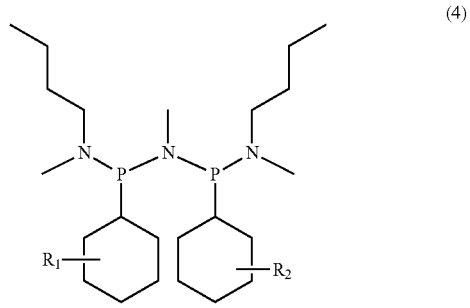
(4)

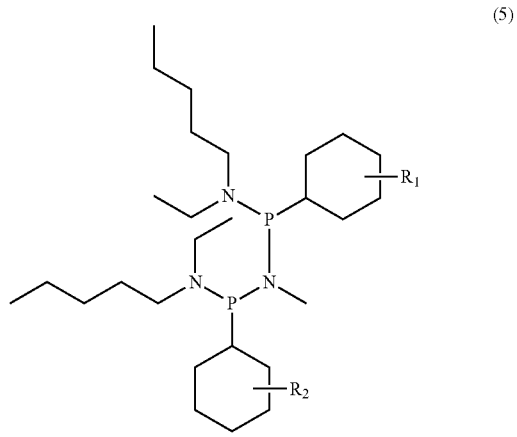
(5)

where $R_1$ and $R_2$ represent alkyl groups such as methyl, ethyl, propyl, isopropyl, butyl, tert-butyl, and pentyl, and the like.

The NPNPN ligand system can be made by synthetic approaches known to those skilled in the art. In some embodiments, ligand (1) is accessible by reaction pathways as shown in Scheme I.

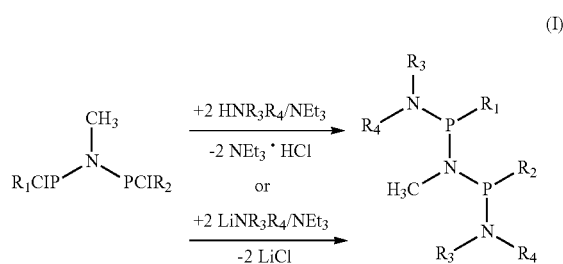

where $R^1$ and $R^2$ are defined above, and $R_3$ is methyl or ethyl and $R_4$ is butyl when $R_3$ is methyl and pentyl when $R_3$ is ethyl.

The chromium species can be an organic salt, an inorganic salt, a coordination complex, or an organometallic complex of Cr(III). In an embodiment, the chromium species is an organometallic Cr(III) species. Non-limiting examples of the chromium species include Cr(III)acetylacetonate, Cr(III) octanoate, $CrCl_3$ (tetrahydrofuran)$_3$, Cr(III)-2-ethylhexanoate, Cr(III)chloride, or any combination thereof. The molar ligand/Cr ratio can be from about 0.5 to 50, about 0.5 to 5, about 0.8 to about 2.0, about 1.0 to 5.0, or preferably from about 1.0 to about 1.5.

The activator (also known in the art as a co-catalyst) can be an aluminum compound. Non-limiting examples of aluminum compounds include trimethylaluminum, triethylaluminum, triisopropylaluminum, triisobutylaluminum, diethylaluminum chloride, ethylaluminum sesquichloride, ethylaluminum dichloride, methylaluminoxane, or a mixture thereof. In some embodiments, the activator can be a modified methylaluminoxane, more preferably MMAO-3A (CAS No. 146905-79-5), which is a modified methylaluminoxane, type 3A, available from Akzo Nobel in toluene solution containing 7% aluminum, which corresponds to an MMAO-3A concentration of about 18%. The molar Al/Cr ratio can be from about 1 to about 1000, about 10 to about 1000, about 1 to 500, about 10 to 500, about 10 to about 300, about 20 to about 300, or preferably from 50 to about 300.

The catalyst composition can further include a solvent. Non-limiting examples of solvents are straight-chain and cyclic aliphatic hydrocarbons, straight-chain olefins, ethers, aromatic hydrocarbons, and the like. A combination comprising at least one of the foregoing solvents can be used. Preferably, the solvent is n-heptane, toluene, or methylcyclohexane or any mixture thereof.

The concentration of the chromium compound in the solvent vary depending on the particular compound used and the desired reaction rate. In some embodiments, the concentration of the chromium compound is from about 0.01 to about 100 millimole per liter (mmol/l), about 0.01 to about 10 mmol/l, about 0.01 to about 1 mmol/l, about 0.1 to about 100 mmol/l, about 0.1 to about 10 mmol/l, about 0.1 to about 10 mmol/l, about 1 to about 10 mmol/l, and about 1 to about 100 mmol/l. Preferably, the concentration of the chromium compound is from about 0.1 to about 1.0 mmol/l.

In some embodiments, the catalyst composition includes Cr(III)acetylacetonate as the chromium compound, Et(n-pentyl)N—P(cyclohexyl)-N(Me)-P(cyclohexyl)-N(n-pentyl)Et as the NPNPN ligand, and MMAO-3A as the activator. In another embodiment, the catalyst composition includes Cr(III)acetylacetonate as the chromium compound, Me(n-butyl)N—P(cyclohexyl)-N(Me)-P(cyclohexyl)-N(n-butyl)Me as the NPNPN ligand, and MMAO-3A as the activator.

B. System for Oligomerization of Olefins to 1-Hexene

The catalyst composition of the present invention can be used in a process for the oligomerization of ethylene to 1-hexene. In an embodiment, the process encompasses contacting ethylene with the catalyst composition under ethylene oligomerization conditions effective to produce 1-hexene. Those skilled in the art will understand that oligomerization of ethylene to produce 1-hexene can be by trimerization of ethylene.

FIG. 1 depicts a schematic for a system to produce 1-hexene. The system 100 can include an inlet 102 for a reactant feed that includes ethylene, a reaction zone 104 that is configured to be in fluid communication with the inlet, and an outlet 106 configured to be in fluid communication with the reaction zone 104 and configured to remove a product stream from the reaction zone. The reactant zone 104 can include the catalyst composition of the present invention. The ethylene reactant feed can enter the reaction zone 104 via the inlet 102. In some embodiments, the ethylene reactant feed can be used to maintain a pressure in the reaction zone 104. In some embodiments, the reactant feed stream includes inert gas (e.g., nitrogen or argon). After a sufficient amount of time, the product stream can be removed from the reaction zone 104 via product outlet 106. The product stream can be sent to other processing units, stored, and/or transported.

System 100 can include one or more heating and/or cooling devices (e.g., insulation, electrical heaters, jacketed heat exchangers in the wall) or controllers (e.g., computers, flow valves, automated values, etc.) that can be used control the reaction temperature and pressure of the reaction mixture. While only one reactor is shown, it should be understood that multiple reactors can be housed in one unit or a plurality of reactors housed in one heat transfer unit.

As discussed above, the process and catalyst composition of the present invention allows for the production of 1-hexene with high selectivity with the LAO product distribution being limited to 1-hexene and 1-octene. High selectivity for 1-hexene is an advantageous feature inasmuch as it leads to higher product purity, thereby circumventing the need for additional purification steps in the separation train. Further advantageous features of the catalyst composition and process include suppression of ethylene polymerization leading to undesirable polymer formation, milder reaction conditions and, as a result, lower capital costs for equipment as well as operational and energy costs. Additionally, a relatively simple, straight-forward process design is possible. The selectivity for 1-hexene is greater than 80 wt. %, 85 wt. %, 90 wt. %, 95 wt. %, or about 100 wt. %, or any range or value therebetween. The purity for 1-hexene can be at least about 99%, or 99.1%, 99.2%, 99.3%, 99.4%, 99.5%, 99.6%, 99.7%, 99.8%, or 99.9%. A purity of at least 99.1% is preferred. In an embodiment, when 1-octene is produced, the weight ratio of 1-octene to 1-hexene can be less than 0.3, or 0 to 0.3, or 0.1, 0.15, 0.2, 0.25 or 0.3 or any range or value there between.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of Ligands 2 and 3

Route A, General Procedure (See, Scheme 1). All manipulations were carried out under inert atmosphere. Bis(chlorophosphino)amine $C_6H_{11}P(Cl)N(CH_3)P(Cl)C_6H_{11}$ (4.60 g, 14 mmol) was dissolved in 20 mL of anhydrous toluene. Appropriate secondary amine (29.4 mmol) and $NEt_3$ (35 mmol) was mixed with 30 mL of anhydrous toluene and cooled down to −10° C. Toluene solution of bis(chlorophosphino)amine was added dropwise to the reaction mixture under inert atmosphere with vigorous stirring. Addition of the reagent resulted in precipitation of white gel-like material. With continuous stirring, solution was left to warm up to 25° C. for 3 hours, then heated to 75° C. and stirred at that temperature for additional 12 hrs. After evaporation of all volatile compounds under vacuum, the residue was taken up in anhydrous hot n-heptane and insoluble material was separated by filtration. Evaporation of the solvent led to pale yellow oil. Purity of the product was verified using $^1H$, $^{13}C$ and $^{31}P$ NMR. If desired, the products can be recrystallized from n-hexane, cyclohexane, n-heptane or n-pentane to increase the purity.

Route B, General Procedure (See, Scheme 1). All manipulations were carried out under inert atmosphere. The appropriate secondary amine (10 mmol) was dissolved in 20 mL of anhydrous n-heptane, cooled down to −10° C. and treated with 5% mol. excess of n-BuLi in n-hexane. The solution was then stirred for 3 hrs letting the temperature raise to 25° C., forming white precipitate. Solid was separated from solution, washed with n-hexane and transferred to the flask with 30 mL of anhydrous $Et_2O$. Resulted suspension was cooled down to −10° C. and solution of bis(chlorophosphino) amine $C_6H_{11}P(Cl)N(CH_3)P(Cl)C_6H_{11}$ (1.61 g, 4.9 mmol) in 30 mL of anhydrous $Et_2O$ was added dropwise to the reaction mixture with vigorous stirring. After the addition, reaction mixture was continuously stirred for 12 hours letting it warm up to 25° C. During the course of the reaction, white solid was formed. Insoluble material was separated by filtration, washed with $Et_2O$ and discarded. Solution and washing liquids were combined and solvent was removed in vacuum, producing pale yellow viscous oil. Purity of the product was verified using $^1H$, $^{13}C$ and $^{31}P$ NMR. If desired, the products can be recrystallized from n-hexane, cyclohexane, n-heptane or n-pentane to increase the purity.

Precursor $(C_6H_{11})P(Cl)N(Me)P(Cl)(C_6H_{11})$ was prepared by the procedure of Jefferson et al. (*J. Chem. Soc. Dalton Trans.* 1973, 1414-1419).

Example 2

Catalyst Composition Preparation and Oligomerization of Ethylene

The reactor, equipped with dip tube, thermowell, mechanical paddle stirrer, cooling coil, control units for temperature, pressure and stirrer speed (all hooked up to a data acquisition system) was prepared for the catalytic run by heating to 130° C. in under vacuum for 4 hours and cooled down by venting with dry nitrogen stream to 30° C. An isobaric ethylene supply was maintained by gas dosing control unit connected to data acquisition system. Ethylene consumption was monitored via pressure loss in the feeding cylinder over time by means of a computerized data acquisition system.

Suitable amounts of the stock toluene solutions of the ligands and Cr(III)acetylacetonate as chromium precursor, at a ligand to Cr ratio of 1.20, were measured and charged to a Schlenk tube under inert atmosphere. A volume of 30 mL anhydrous n-heptane was introduced in stainless steel pressure reactor and warmed up to desired reaction temperature. After temperature of the reactor become stable, reactor was pressurized to 30 bar of ethylene and left for 30 min with continuous mechanical stirring. After that time, pressure was reduced to 0.2 bar and appropriate amount of 0.3M stock solution of MMAO-3A in anhydrous n-heptane was introduced in the reactor through the charging port, providing Al to Cr ratio of 300. Stirring was continued for 10 min. Following that, mixture of Cr and ligand solutions was introduced into the reactor through the charging port.

Immediately after introduction of the catalyst in the reactor, pressure was increased to 30 bar. Standard reaction conditions are: pressure of ethylene of 30 bar, T=45° C., stirrer speed of 450 RPM. After 1 hour catalytic run, ethylene supply was cut and reactor temperature lowered to 5° C. Ethylene from the reactor was vented to the pressure of 0.2 bar. The reaction was quenched with 0.3M HCl/iso-Propanol mixture. It should be noted that it is also possible to quench the reaction with different agents, such as Decan-1-ol, 2-EHA, 20% wt. NaOH in water. Liquid products were analyzed using gas chromatography with a known amount of toluene as internal standard. Any insoluble by-products, i.e., waxes, polyethylene, were filtered, dried, and weighed. Table 1 shows the results of ligand

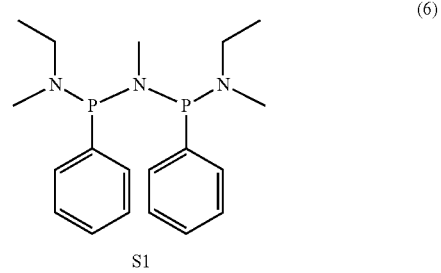

S1 (6)

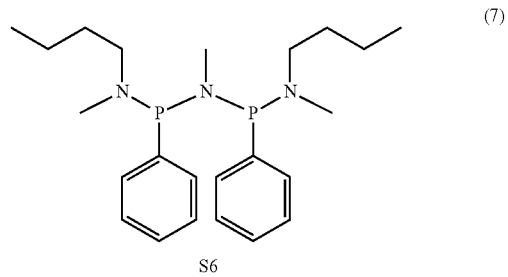

S6 (7)

S12 catalyst includes the ligand is that shown as structure (2) above (having two methyl and two n-butyl substituents).

TABLE 1

| Catalyst | Activity (kg/ $g_{Cr}$ * h) | % wt. C6 (1-hexene, %) | % wt. C8 (1-octene, %) | Solvent Insoluble % wt. |
|---|---|---|---|---|
| S12 (Run 1) | 56.50 | 85.62 (99.45) | 9.69 (95.80) | 2.28 |
| S12 (Run 2) | 169.00 | 87.99 (99.92) | 5.71 (99.95) | 0.53 |
| S6 (Comparative; Structure (7)) | 179.15 | 21.55 (79.20) | 76.86 (99.41) | 0.32 |
| S1 (Comparative; Structure (6)) | 95.45 | 40.10 (76.78) | 58.11 (96.13) | 1.09 |

Table 1 summarizes the results of ethylene oligomerization experimental runs performed under these standard conditions and using catalyst systems prepared with the catalyst S12 with ligand (2) and a comparative catalysts. The Table shows the respective selectivities for C6, C8, and solvent insolubles in wt. % in the liquid phase. Numbers in parentheses denote the selectivities of the respective linear alpha-olefin in the overall C6/C8 fraction. These LAO purities are generally advantageously high. The comparative catalyst differs from catalyst S12 in that catalyst S12 includes the ligands shown in Formula (2) in this specification, while the comparative catalysts include the ligands shown in Formula (6) and (7) have two phenyl groups replacing the two cyclohexyl groups in Formula (2). Two runs are shown for S12 catalyst. It was observed that a second consecutive run typically demonstrates better performance than the initial run. Although not wanting to be bound by theory, it is suspected that this quite typical behavior is likely attributable to the reactor being dried and cleaned during the first run. Notwithstanding the improvement from the first and second run, the data clearly demonstrates the different behavior in comparison to S12 and S6 species, which have aromatic groups on the two phosphorus atoms.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A catalyst composition for the oligomerization of ethylene to 1-hexene, the catalyst composition comprising:
   a chromium (III) species; and
   a ligand having the formula of:

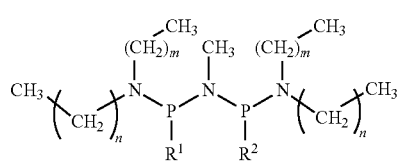

where $R^1$ and $R^2$ are the same or different and are selected from the group consisting of (i) $C_3$ to $C_4$ non-cyclic aliphatic groups, (ii) $C_5$ to $C_7$ aliphatic groups which may be cyclic or non-cyclic, linear or branched, substituted or unsubstituted, and (iii) any combination thereof; and,
wherein n is 0 or 1, and m=n+3.

2. The catalyst composition of claim 1, wherein $R^1$ and $R^2$ are each independently a cyclic hydrocarbon group, a substituted cyclic hydrocarbon group, a linear hydrocarbon group or a branched hydrocarbon group having 1 to 10 carbon atoms.

3. The catalyst composition of claim 2, wherein $R^1$ and $R^2$ are each a cyclohexyl group.

4. The catalyst composition of claim 3, wherein n is 0, and the ligand has the structure of:

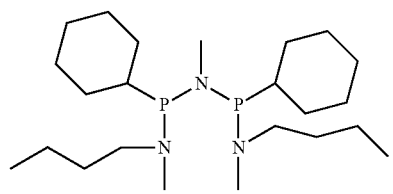

5. The catalyst composition of claim 3, wherein n is 1 and the ligand has the structure of:

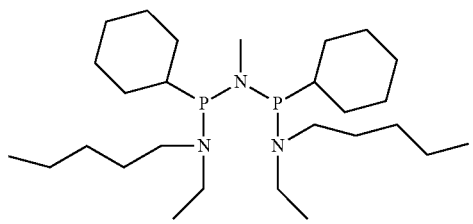

6. The catalyst composition of claim 1, wherein the composition further comprises an activator or co-catalyst.

7. The catalyst composition of claim 6, wherein the activator or co-catalyst is a methylaluminoxane compound.

8. The catalyst composition of claim 6, wherein the activator or co-catalyst is a methyl iso-butyl aluminum oxide compound.

9. The catalyst composition of claim 1, wherein the chromium (III) species is selected from the group consisting of chromium (III) acetylacetonate, Cr(2,2,6,6,-tetramethyl-3,5-heptadionate)$_3$, chromium(III)2-ethylhexanoate, chromium trichloride; tris-tetrahydrofuran, (benzene)tricarbonyl chromium, chromium (III) octanoate and chromium (III) naphthenate.

10. The catalyst composition of claim 1, wherein one or both of $R^1$ and $R^2$ are selected from the group consisting of iso-propyl and tert-butyl.

11. A process to produce 1-hexene from ethylene, the process comprising contacting a reactant stream comprising an olefin source with a solution comprising the catalyst composition of claim 1 to produce a oligomer composition comprising 1-hexene.

12. The process of claim 11, wherein the solution comprises a solvent.

13. The process of claim 12, wherein the solvent is a saturated hydrocarbon.

14. The process of claim 13, wherein the solvent is n-hexane, methylcyclohexane, or a mixture thereof.

15. The process of claim 11, wherein the oligomer product further comprises 1-octene and a selectivity for 1-hexene is greater than 99%, and a weight ratio of 1-octene to 1-hexene is less than 0.15.

16. The process of claim 15, wherein the ligand comprises:

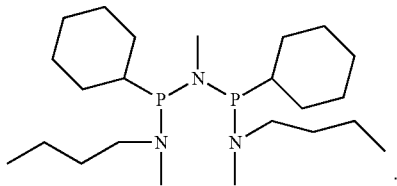 [SMILES: CCCCN(C)P(C1CCCCC1)N(C)P(C1CCCCC1)N(C)CCCC]

17. The process of claim 15, wherein the solution further comprises an activator or co-catalyst.

18. The process of claim 11, wherein the catalyst composition comprises the chromium (III) species, an activator or co-catalyst and the ligand has the structure of:

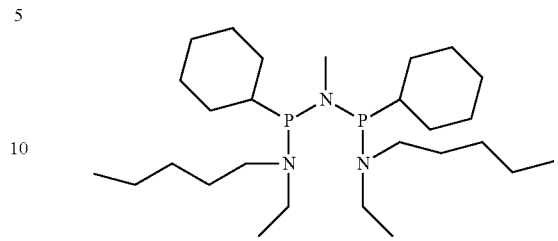

19. The process of claim 11, wherein the contacting comprises a temperature of 15° C. to 100° C.

20. The process of claim 11, wherein the contacting comprises a pressure of at least 2 MPa or 2 to 20 MPa.

* * * * *

UNITED STATES PATENT AND TRADEMARK OFFICE
CERTIFICATE OF CORRECTION

PATENT NO. : 11,247,201 B2
APPLICATION NO. : 17/292285
DATED : February 15, 2022
INVENTOR(S) : Abdulaziz Al-Nezari et al.

It is certified that error appears in the above-identified patent and that said Letters Patent is hereby corrected as shown below:

In the Claims

In Column 16, Claim 5, insert a space between "1" and "and."

Signed and Sealed this
Seventh Day of June, 2022

Katherine Kelly Vidal
*Director of the United States Patent and Trademark Office*